Aug. 8, 1967 D. L. ARMSTRONG Plant Pat. 2,758
NECTARINE TREE
Filed May 20, 1966
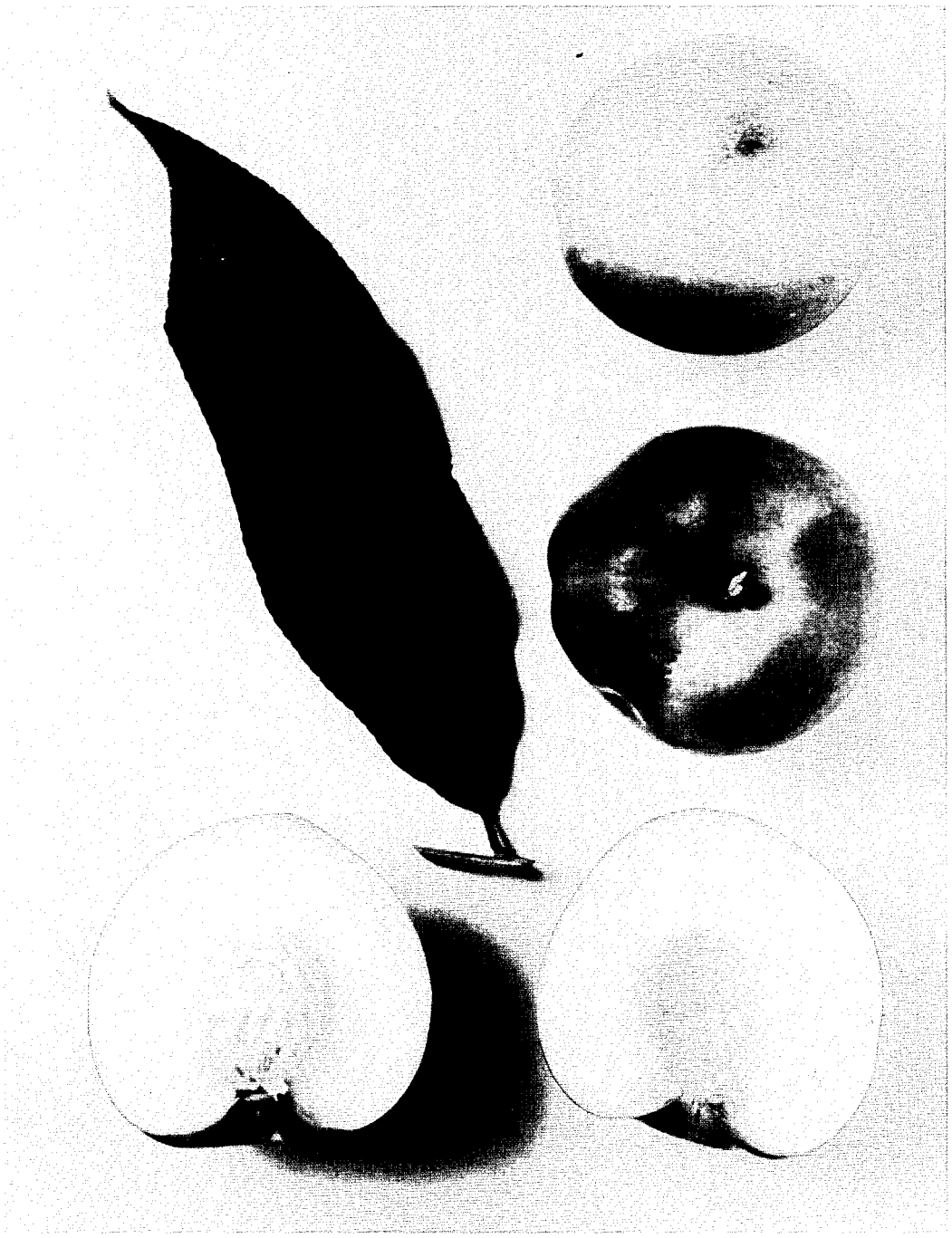
Inventor.
D. L. Armstrong
By: Robb & Robb
Attorneys.

United States Patent Office

Plant Pat. 2,758
Patented Aug. 8, 1967

2,758
NECTARINE TREE

David L. Armstrong, Ontario, Calif., assignor to Armstrong Nurseries, Inc., Ontario, Calif., a corporation of California Filed May 20, 1966, Ser. No. 551,813
1 Claim. (Cl. Plt.—41)

The present invention relates to a new and distinct variety of nectarine tree which was originated by me by crossing an unnamed and unpatented nectarine variety with an unnamed and unpatented peach variety, the former being the seed parent and the latter being the pollen parent. The seed parent was the result of an extended series of crosses going back two and three generations to the peach varieties "Babcock" (unpatented), "July Elberta" (Plant Patent No. 15) and "Chinese Dwarf" (unpatented) and the nectarine varieties "Boston" (unpatented) and "Gold Mine" (unpatented), while the pollen parent was the result of a cross of nectarine variety "Panamint" (Plant Patent No. 1,100) and peach variety "Springtime" (Plant Patent No. 1,268).

The general objective of this breeding was to produce a new nectarine variety which has an early fruit ripening habit and produces yellow-fleshed fruit of good quality. This objective was fully achieved, along with other desirable features, as evidenced by the following unique combination of characteristics which are outstanding in the new variety and distinguish it from its parents, as well as from all other varieties of which I am aware:

(1) A vigorous tree habit, with a chilling requirement approximately equal to that of "Springtime" peach;

(2) Production of large fruit crops;

(3) A very early fruit ripening habit as compared with other available nectarine varieties, and generally, a few days ahead of "Robin" peach (Plant Patent No. 529), about one week after "Springtime" peach, and about one week before "Armred" nectarine (Plant Patent No. 2,580);

(4) Attractive and uniform fruit having a nearly round shape, with no beak;

(5) A characteristic nectarine skin smoothness and lack of pubescence;

(6) Yellow-fleshed fruit, with no trace of red color at the stone, but although having a strong tendency of the flesh to adhere to the stone because of the early ripening habit, the fruit being essentially freestone when fully ripe;

(7) An attractive fruit coloring, with the heavy and often bright red blush nearly over all; and (8) Particularly good quality of the fruit, with a sweet, balanced flavor.

The unnamed seed parent was a white-fleshed, freestone nectarine ripening in the general period of a few days after "Redhaven" peach (unpatented) but the fruit was of medium size, nearly round and had a heavy red skin color, while the tree was productive, with a medium chilling requirement. The new variety is distinguished from this parent primarily by having yellow-fleshed fruit, with a ripening habit several weeks earlier.

The unnamed pollen parent was a yellow-fleshed, freestone peach, ripening in the general period of "Robin" peach, with the fruit being of medium size and nearly round shape, with a good red skin color. The new variety differs from this parent by being a nectarine instead of a peach, and the fruit ripens a few days earlier than the peach fruit of the parent.

In comparison with its ancestor "Boston," which has a late mid-season ripening habit, the new variety is earlier ripening and the fruit has a much heavier red skin color.

As compared with its ancestor "Gold Mine" nectarine, which bears white-fleshed fruit and ripens in mid-season, the new variety bears yellow-fleshed fruit and ripens earlier.

The new variety is distinguished from its ancestor "July Elberta" peach by being a nectarine, with a ripening habit about five weeks earlier and the fruit having a much heavier red skin color as compared with the relatively little red skin color of "July Elberta."

The new variety is distinguished from "Sunrise" nectarine by ripening at least ten days earlier, and having less red skin speckling than the fruit of "Sunrise."

In comparison with its ancestor "Armred" nectarine, the new variety ripens about a week earlier and the fruit usually has a somewhat brighter and more heavy skin color.

Asexual reproduction of my new variety by budding, as performed by me at Wasco, Calif., shows that the foregoing characteristics and distinctions come true to form and are established and transmitted through succeeding propagations.

The accompanying drawing shows typical specimens of the fruit and foilage of my new nectarine variety, with both exterior and sectional views of the fruit being shown, the latter exposing the stone in one half-section and the cavity in the other half-section, with all of the views being depicted in color as nearly true as it is reasonably possible to make the same in a color illustration of this character.

The following is a detailed description of my new variety, as based upon observations of specimens grown at Wasco, Calif., with color terminology in accordance with Robert F. Wilson's Horticultural Color Chart (hereinafter abbreviated as (W)) and Ridgway's Color Standards and Nomenclature (hereinafter abbreviated as (R)), except where general color terms of ordinary dictionary significance are obvious:

*Tree*

Habit: Vigorous; upright-spreading.

Chilling requirement: Moderate, near that of "Springtime" peach.

Fruit production: It bears a heavy crop; considerable thinning is necessary.

Current growth:

*Surface texture.*—Smooth at first (with lenticels small and minute; with age, some larger, cracked, slightly raised lenticels appear toward the base of the more vigorous shoots.

*Color.*—At first green, or reddish on exposed surfaces, with lenticels appearing as small, near white dots; all becoming more brown with age.

Two-year wood:

*Surface texture.*—Generally smooth, with slightly raised, irregular, longitudinal striations and numerous lenticels.

*Color.*—Brown.

Old wood:

*Surface texture.*—Generally smooth, with moderate number of large, raised lenticels, and some small longitudinal fissures.

*Color.*—From grey to greyish-brown or reddish brown on more exposed surfaces.

Leaves:

*Size.*—From 4½ to 6½ inches long; from 1¼ to 1¾ inches wide.

*Shape.*—Lanceolate, with apex acuminate.

*Color (mature).*—Upper surface—between Jade Green, Plate XXXI (R) and Cress Green, Plate XXXI (R). Under surface—near Light Elm Green, Plate XVII (R).

*Petiole.*—Medium length; from thick to medium thickness.

*Margin.*—Finely serrate; glandular.

*Glands.*—Mixed; mostly reniform, with a few globular glands borne on some leaves; medium size; usually from 3 to 5 in number; borne both on the petiole and on the base of the blade; some leaves have only reniform glands; as when globular glands are present, they are present only in numbers of 1 or 2 per leaf, and they appear only on the petiole, and are usually near the point of attachment of the leaf to the stem.

Vegetative buds:

*Size.*—Small.

*Shape.*—Ovoid, unless compressed between flower buds.

*Scales.*—Pubescence thick, and moderate length.

*Color.*—Dark brown.

*Flowers*

Dates first and full bloom: Over a six-year period of observation, varied from February 20 to March 6 for first bloom, and from March 2 to March 16 for full bloom, due to weather variations from year to year.

Dormant flower buds:

*Shape.*—Ovoid.

*Scales.*—Pubescent.

*Color.*—Dark brown, with pubescence giving a whitish effect.

Size (when fully open): Showy; about 1½ inches in diameter.

Petalage: Single; usually 5 petals.

Form: Cupped.

Color (open flower): Between Rose Pink, Plate 427/3, page 126 (W) and Rose Pink, Plate 427/2, page 126 (W), with age darkening toward center to between Phlox Pink, Plate 625/2, page 77 (W) and Phlox Pink, Plate 625, page 77 (W).

Ripening dates: Generally ripens in late May at Wasco, Calif.; over six years of observation, the dates of first ripening ranged from May 23, to May 30; it ripens in the general period of 4 to 10 days after "Springtime" peach, 1 to 4 days ahead of "Robin" peach and about one week ahead of "Armred" nectarine.

Maturity when described: Eating ripe.

Size: Generally from small to medium size.

*Axial diameter.*—From 1⅞ to 2¼ inches.

*Transverse diameter in suture plane.*—From 1¾ to 2¼ inches.

*Transverse diameter at right angles to suture plane.*—From 1⅞ to 2¼ inches.

Form: Relatively uniform; between globose and broadly ovoid.

Suture: Generally shallow; extending usually over nearly entire circumference; slight depression beyond pistil point.

Ventral surface: Rounded; sometimes slightly lipped toward apex.

Stem cavity: Usually rounded; from circular to slightly elongated in suture plane; with suture showing usually on both sides.

*Depth.*—About ¼ inch.

*Width.*—From about ⅜ to ½ inch.

Base: Rounded.

Apex: From rounded to somewhat depressed; pistil point short and apical.

Stem: Medium caliper; glabrous; medium adherence to stone. Length—about ¼ inch.

Skin:

*Thickness.*—Thin.

*Texture.*—Between medium and tender.

*Tenacity to flesh.*—Usually free.

*Pubescence.*—None; characteristic smooth skin of the nectarine.

*Color.*—Ground color varies from near Indian Yellow, Plate 6/2, page 6 (W) to near Cadmium Orange, Plate 8/2, page 8 (W); heavily blushed nearly overall with between near Brick Red, Plate 016, page 106 (W) and near Garnet Brown, Plate 00918/2, page 192 (W).

Flesh:

*Quality.*—Medium firm; melting; fine texture.

*Aroma.*—Pronounced.

*Flavor.*—Good balance between sugar and acid.

*Color.*—Between Saffron Yellow, Plate 7/2, page 7 (W) and Sulphur Yellow, Plate 1/2, page 1 (W); surface of pit cavity varying from near Straw Yellow, Plate 604/1, page 67 (W) to near Chinese Yellow, Plate 606/2, page 68 (W).

Stone:

*Tenacity of flesh.*—Basically free, but because of early ripening, stone adheres to flesh along both dorsal and ventral edges until the fruit is fully ripe.

*Size.*—From medium to small; length from about ⅞ to 1⅛ inches; width from ¾ to 1 inch; thickness from ⅝ to ¾ inch.

*Form.*—Ovoid.

*Base.*—Usually oblique.

*Hilum.*—Oval.

*Apex.*—Obtuse.

*Sides.*—Usually equal; curved on right and left sides; irregularly furrowed toward apex; pitted toward base.

*Ventral edge.*—Thin; generally without wing.

*Dorsal edge.*—Between medium and narrow; with shallow narrow groove; ridges on either side interrupted.

*Color.*—Between Warm Buff, Plate XV (R) and Cream Buff, Plate XXX (R).

I claim:

A new and distinct variety of nectarine tree of the yellow-fleshed, freestone fruit-bearing type, substantially as herein shown and described, characterized particularly as to novelty by the unique combination of a vigorous tree habit, with a chilling requirement approximately equal to that of "Springtime" peach, production of large fruit crops, a very early fruit ripening habit as compared with other available nectarine varieties, and generally a few days ahead of "Robin" peach (Plant Patent No. 529), about one week after "Springtime" peach, and about one week before "Armred" nectarine (Plant Patent No. 2,580), attractive and uniform fruit having a nearly round shape, with no beak, a characteristic nectarine skin smoothness and lack of pubescence, yellow-fleshed fruit, with no trace of red color at the stone, but although having a strong tendency of the flesh to adhere to the stone because of the early ripening habit, the fruit being essentially freestone when fully ripe, an attractive fruit coloring, with a heavy and often bright red blush nearly over all and particularly good quality of the fruit with a sweet, balanced flavor.

No references cited.

ABRAHAM G. STONE, *Primary Examiner.*

ROBERT E. BAGWILL, *Examiner.*